(12) United States Patent
Léger et al.

(10) Patent No.: US 6,574,800 B1
(45) Date of Patent: Jun. 10, 2003

(54) GARMENTS FOR SUPPORT, CONCEALMENT, AND ACCESSIBILITY OF MEDICAL DRAINAGE APPARATUS

(76) Inventors: Jayle G. Léger, 286 N. Silver La., Sunderland, MA (US) 01375; Lois P. Jenner, P.O. Box 1613, 184 Standish St., Duxbury, MA (US) 02331

( * ) Notice: Subject to any disclaimer, the term of this patent is extended or adjusted under 35 U.S.C. 154(b) by 0 days.

(21) Appl. No.: 09/852,583

(22) Filed: May 10, 2001

Related U.S. Application Data (60) Provisional application No. 60/203,739, filed on May 11, 2000.

(51) Int. Cl.$^7$ ............................. A41D 1/22; A61M 25/00
(52) U.S. Cl. .................................. 2/114; 2/69; 604/174
(58) Field of Search ........................ 2/114, 69, 104–106, 2/94, 85, 93, 95, 80, 83, 1, 115, 249–253; 604/174, 179, 345

(56) References Cited

U.S. PATENT DOCUMENTS

| | | | | |
|---|---|---|---|---|
| 1,247,404 A | * | 11/1917 | Hyde ............................. | 2/106 |
| 2,883,673 A | * | 4/1959 | Solomon ........................ | 2/253 |
| 4,570,268 A | * | 2/1986 | Freeman ........................ | 2/114 |
| 4,683,594 A | * | 8/1987 | Feinberg ........................ | 2/105 |
| 5,097,535 A | * | 3/1992 | Dye et al. ........................ | 2/69 |
| 5,142,702 A | * | 9/1992 | Piloian ........................... | 2/102 |
| 5,228,140 A | * | 7/1993 | Baustin ............................ | 2/93 |
| 5,257,956 A | | 11/1993 | Ewen | |
| 5,392,466 A | * | 2/1995 | Chou et al. ..................... | 2/114 |
| 5,429,593 A | | 7/1995 | Matory | |
| 5,429,623 A | | 7/1995 | Dessel | |
| 5,439,456 A | | 8/1995 | Fabricant | |
| 5,553,323 A | * | 9/1996 | Chou et al. ..................... | 2/114 |
| 5,638,549 A | * | 6/1997 | Thomas .......................... | 2/247 |
| 5,643,233 A | | 7/1997 | Turner | |
| 5,652,961 A | * | 8/1997 | Knight-Yurt .................... | 2/114 |
| 5,713,292 A | * | 2/1998 | Wong ............................. | 2/247 |
| 5,716,344 A | | 2/1998 | Kiel | |
| 5,799,330 A | * | 9/1998 | O'Donoghue-Kitt ........... | 2/114 |
| 5,950,238 A | | 9/1999 | Klein | |
| 5,980,499 A | | 11/1999 | Ekey | |
| 5,991,923 A | * | 11/1999 | Maria .............................. | 2/83 |
| 6,032,289 A | * | 3/2000 | Villapiano ...................... | 2/102 |

OTHER PUBLICATIONS

"Pouch Pockets™ Recovery Wear," printed from web site http://www.pouchpockets.com, having a date as early as Jan. 1, 2002.
"Features" printed from web site http://www.pouchpockets.com, having a date as early as Jan. 1, 2002.

* cited by examiner

*Primary Examiner*—Gloria M. Hale
(74) *Attorney, Agent, or Firm*—Theresa A. Lober (57) ABSTRACT

The invention provides a garment including a torso portion of an extent sufficient to encircle a garment wearer's torso and arm openings provided in the torso portion. Generally vertical and cooperating front torso portion edges are included, providing a vertical front closure of the torso portion. At least one opening in the torso portion is provided. This garment opening is of an extent that is sufficient to accommodate passage of a fluidic tube and a corresponding fluidic receptacle through the opening and to accommodate positioning of at least one fluidic tube to extend from the through the garment opening. At least one fluidic receptacle support is located on an outside surface of the torso portion. The fluidic receptacle support has a receptacle support surface below a point at which a corresponding fluidic tube would be positioned to extend through a corresponding garment opening. This garment configuration enables self-positioning and maintenance of drainage tubes and receptacles by the garment wearer while at the same time allowing for concealment of the tubes and receptacles, thereby aiding in patient recovery.

31 Claims, 10 Drawing Sheets

GARMENTS FOR SUPPORT, CONCEALMENT, AND ACCESSIBILITY OF MEDICAL DRAINAGE APPARATUS

This application claims the benefit of U.S. Provisional Application No. 60/203,739, filed May 11, 2000, the entirety of which is hereby incorporated by reference.

BACKGROUND OF THE INVENTION

This invention relates to techniques for accommodating fluidic tube apparatus, such as drainage apparatus, often required for patients following a thoracic medical procedure such as surgery, e.g., a mastectomy, axillary node dissection, plastic surgery, or a procedure such as chemotherapy, or other thoracic procedure. Many medical thoracic procedures, and in particular surgical procedures that require the removal of tissue, e.g., in a mastectomy or axillary node dissection, are traumatic to the human body. The removal of a large amount of tissue in such a procedure tends to create in the body a cavity in which fluid collects. To prevent swelling and infection that could result from fluid remaining in the body, it is common practice to insert a drainage tube into the cavity at a point along the incision. This drainage tube, which is typically perforated at both ends and is often several inches long, extends to a collection receptacle, e.g., a plastic bulb, for collection of fluid drained by the tube. The suction created by the drainage tube is understood to aid in binding the skin of the cavity to the muscle until the incision heals.

The number of drainage tubes and collection receptacles required can vary from as few as one to as many as six, depending on the type of medical procedure and the amount of fluid expected to be produced by the body. The time required for drainage of the produced fluid can be as short as one week or as long as several weeks after the medical procedure. Historically, individuals undergoing such a medical procedure remained hospitalized until the drainage tubes were no longer required. But with the advent of managed medical care, hospitals frequently discharge patients on the same day or one to two days following a procedure such as surgery. Once a patient has received instruction on how to attend to the drainage apparatus; i.e., how to empty the collection receptacles, measure collected fluid, and keep a written record for the physician, the patient is discharged to self-care.

Outside the hospital setting, the patient is left to figure out how to adapt to life with the often painful, annoying, and cumbersome appendages of the drainage apparatus. However many drainage tubes and collection receptacles are employed, and for however long they are required, the management of the tubes and collection receptacles pose numerous and varied problems for the patient. Specifically, the tubes and receptacles can be a constant source of aggravation to the patient in that they restrict mobility, are cumbersome to wear, and must be monitored and emptied frequently, thus requiring ready and easy access. Furthermore, because of the bulk of the drainage apparatus, and the discomfort at the incision site, conventional clothing often cannot be worn.

To enable support of drainage apparatus at a location adjacent to the patient's body, various methods and devices have been historically employed and proposed. In one common technique, the collection receptacle is pinned to the gown worn by the patient or to the bandage covering the incision. This method, while not very comfortable, is effective in the hospital when an open gown is often worn. However, this approach causes the patient to be more dependent on assistance in manipulating the pin while holding the drainage receptacle in place during the pinning. This approach has the further disadvantage of the sharp end of the pin possibly becoming unhooked and pricking the patient, causing additional pain and discomfort. Moreover, outside the hospital, where conventional, yet constricting, clothing is worn, use of such means to support collection receptacles and drains is awkward and impractical due to their bulk and inaccessibility for maintenance.

In another common technique, the drainage tubes and collection receptacles are taped directly to the torso of the individual. But because the drainage tubes must be repeatedly untaped and retaped to empty the collection receptacle, the tape often loses its adhesiveness. Consequently, when the drainage tubes are in use, the tape can come undone at an inopportune time, causing the weight of the fluid in the collection receptacles to pull on the tubes, inflicting pain. Also, because the drainage tubes are taped to the body, which is usually covered by some form of clothing, they are not easily and readily accessible for maintenance purposes. The awkwardness, discomfort, and impracticality of these common approaches are only compounded when multiple sets of tubes and receptacles are required to be worn by the patient.

Other proposed approaches for supporting medical drainage apparatus have required various features that frequently are impractical. For example, in U.S. Pat. No. 5,716,344 there is proposed the use of a belt secured around the torso for supporting a drainage receptacle. The receptacle is supplied with a plastic loop through which the belt can be inserted for supplying support. Similarly, in U.S. Pat. No. 5,439,456, there is proposed the use of a band encircling a leg for supporting a drainage receptacle. Fasteners on the band connect to and hold the receptacle on the band. In U.S. Pat. No. 5,643,233, a pouch, for carrying a drainage receptacle, is provided attached to a belt worn around the torso. In U.S. Pat. No. 5,980,499, a plurality of pockets are provided attached to a belt for carrying multiple drainage receptacles.

While these various devices do serve to support a drainage apparatus adjacent to the body, they do not assist in or enhance the patient's adjustment to post-hospital life and self-care with drainage apparatus in-place. All of these proposed devices are required to be worn under clothing. But the bulkiness of the apparatus, the discomfort and swelling at the surgical site, and restriction of mobility are all accentuated when the drainage apparatus is worn under conventional clothing. The necessity of disrobing to access and maintain the drains increases the recovering patient's discomfort and decreases the patient's ability to function independently.

There have also been proposed various configurations of compression and other undergarments that accommodate drainage apparatus. For example, in U.S. Pat. No. 5,429,593, there is proposed a compression dressing having a cut out portion, at the lower edge of the dressing, through which drainage tubes can be supplied. A loop on the dressing above the aperture, high on the torso, is supplied for holding the drainage receptacle against the dressing. Although this configuration maintains the receptacle adjacent the body, its elevated placement of the receptacle can inhibit fluid flow from the incision site to the receptacle, increasing the risk of infection. Finally, in U.S. Pat. No. 5,257,956, there is proposed a compression vest having an aperture, under an arm location, through which drainage tubes can be supplied. No support of the drainage receptacle is supplied in this design. In addition, like the belt and band configurations described above, these configurations also suffer in that they both are undergarments.

It is thus found that the various techniques and configurations commonly employed for support of drainage and other fluidic apparatus fail to meet the needs of a patient convalescing out of the hospital. The drainage apparatus must be supported while at the same time permitting easy access for frequent maintenance of the collection receptacles. Heretofore, this has not been achievable in a configuration enabling conventional-style clothing that can be worn home from the hospital, while convalescing, and outside the home when attending medical appointments and doing errands.

SUMMARY OF THE INVENTION

The invention provides garments that can be worn as top clothes and that provide support and access to fluidic apparatus on the outside of the garments, while allowing for fashion, modesty, and discretion during a recovery process. The garments include a torso portion of an extent sufficient to encircle a garment wearer's torso and arm openings provided in the torso portion. Generally vertical and cooperating front torso portion edges are included, providing a vertical front closure of the torso portion. At least one opening in the torso portion is provided. This garment opening is of an extent that is sufficient to accommodate passage of a fluidic tube and a corresponding fluidic receptacle through the opening. The garment opening extent is also sufficient to accommodate positioning of at least one fluidic tube to extend through the garment opening. At least one fluidic receptacle support is located on an outside surface of the torso portion. The fluidic receptacle support has a receptacle support surface which is vertically below a point at which a corresponding fluidic tube would be positioned to extend through a corresponding garment opening.

This garment configuration enables self-access, positioning, and maintenance of drainage tubes and receptacles by the garment wearer, and overcomes the limitations of prior drainage support techniques that failed to allow a recovering patient to have access to drainage apparatus while at the same time concealing the apparatus.

In embodiments provided by the invention, the garment opening is located at a position around the torso portion corresponding to location of a garment wearer's incision at which the fluidic tube is initiated, and the garment opening is located on the torso portion below the garment wearer's incision location. One or more garment opening fasteners can be provided at a point along the garment opening to close the opening around a fluidic tube positioned to extend through the opening. The garment opening fastener can be provided along the garment opening to substantially fully close the opening. One or more fluidic tube fasteners can be located on the outside surface of the torso portion of the garment, provided with a tab to secure at least one fluidic tube to the torso portion. The fluidic tube fastener can be located at a point along the garment opening. The garment opening can be located at a point along a seam of the torso portion.

In embodiments provided by the invention, the garment opening is located at a position around the torso portion that is self-accessible by the garment wearer. Sleeve portions can be provided connected to the torso portion. The sleeve portions are preferably connected to the torso portion at a drop-shoulder sleeve opening. A kick pleat can be located at a back region of the torso portion. In further embodiments provided by the invention, a front yoke is provided having a gathering located above a point generally corresponding to the bust line of the garment wearer. The cooperating front torso portion edges can include one or more fasteners at the front closure of the torso portion. The cooperating front torso portion edges can be of sufficient horizontal extent to horizontally overlap at the front closure of the torso portion.

The fluidic receptacle support can be provided as, e.g., a compartment, pouch, sleeve, or pocket on an outside surface of the torso garment portion. Considering a support pocket, the pocket can be provided as a slanted pocket, including reinforced pocket seam stitching. The pocket can extend sufficiently over the torso portion outer surface to support and substantially conceal a fluidic receptacle or receptacles. One or more fluidic tube fasteners can be located in the support pocket, including a tab to secure at least one fluidic tube to the torso portion. Preferably, the pocket includes a pocket bottom that is located on the garment torso portion vertically below a point at which a corresponding fluidic would be positioned to extend through a corresponding garment opening. The support pocket can extend over the torso portion a distance sufficient to cover at least a portion, or substantially all of, the corresponding garment opening. The support pocket can further be configured to include a storage pocket on top of the support pocket, and can include an interior surface that is impervious to fluid.

The garments of the invention are particularly well suited for use by female patients who have undergone thoracic surgery such as, e.g., chest, breast, or underarm surgery. The garments are not, however, limited to such procedures. Indeed, the garments of the invention can be advantageously employed in conjunction with any medical procedure, thoracic or otherwise, that requires the support of a drainage apparatus attached to the body. Furthermore, the garments of the invention can be advantageously employed for supporting apparatus other than drainage apparatus, such as chemotherapy apparatus, e.g., for supporting a chemotherapy supply to a port attached to the body. It is therefore to be understood that the garments of the invention are applicable to a wide range of conditions and apparatus, and can easily be adapted for use by youths and male as well as female patients. Furthermore, the ability to convert the garment openings to conventional seams extends the functionality of the garment to the entire treatment and recovery period, and beyond.

Other applications, features, and advantages of the invention will be apparent from the following description and associated drawings, and from the claims.

DETAILED DESCRIPTION OF THE INVENTION

Figure 1:
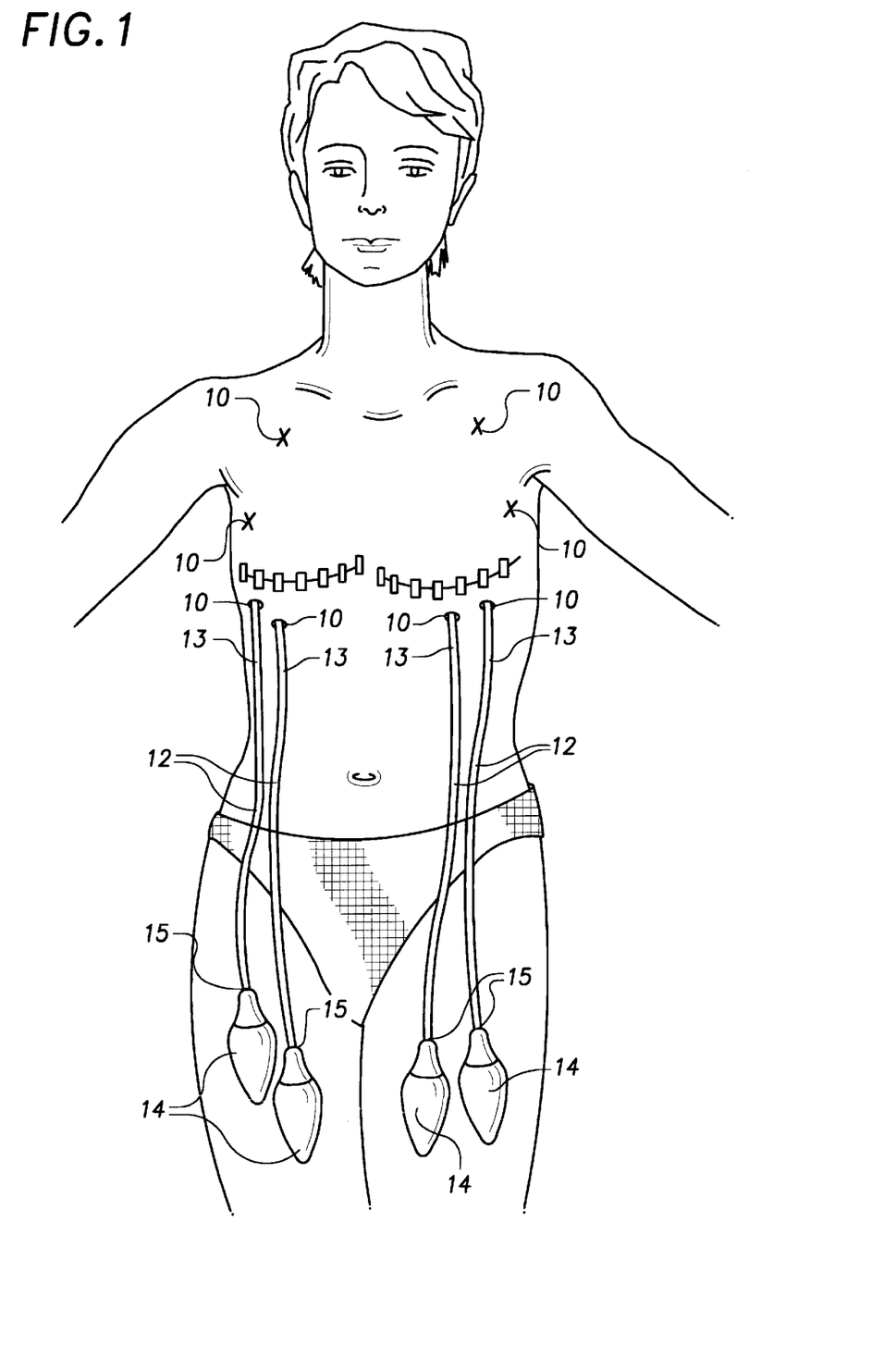
FIG. 1 is a front perspective view of a female patient's body after undergoing thoracic surgery, including several sets of drainage apparatus, attached to the body, that can be supported by the garments of the invention.

Referring to FIG. 1 there is shown a female patient's body, postoperative from a thoracic medical procedure, e.g., a surgical procedure, resulting in one or more surgical incision sites 10, several examples of which are illustrated. At each of the incision sites, here four sites as an example, there is attached a bodily fluid drainage apparatus. The drainage apparatus includes a drainage tube 12 having a first end 13 positioned within the body at an incision site 10, for draining excess fluid from the body cavity at the incision site. A drainage collection receptacle 14, such as a fluid collection bulb, is provided attached at a second end 15 of the drainage tube 12 and in fluid flow communication with the second tube end 15. The collection bulb 14 serves to retain fluid drained from the body cavity through the drainage tube. Under typical circumstances, the drainage collection bulb must be periodically emptied of its fluid, the fluid measured, and a record kept of the fluid flow rate to inform the physician of the drainage apparatus performance as well as the patient's recovery condition.

Figure 2:
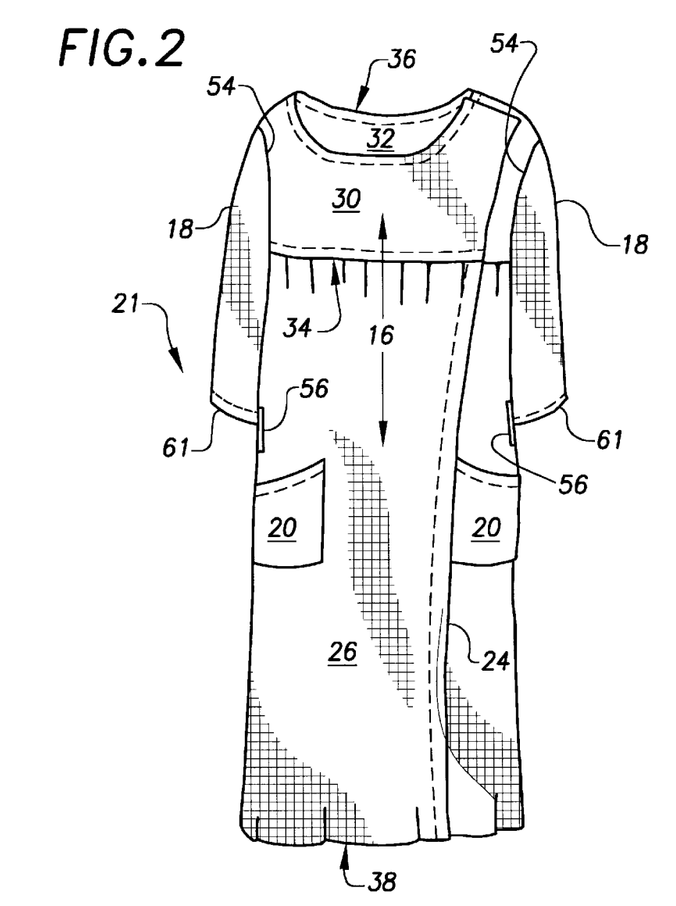
FIG. 2 is a front perspective view of an example house coat garment provided by the invention.
Figure 3:
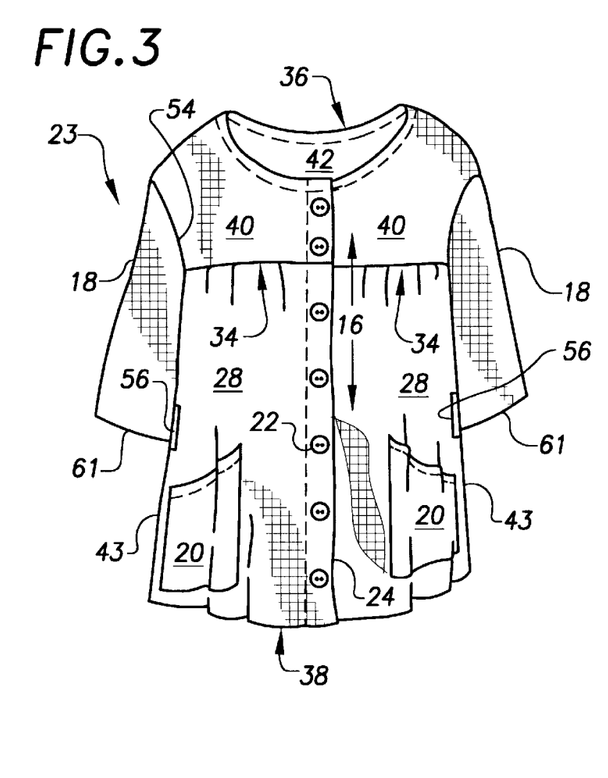
FIG. 3 is a front perspective view of an example top garment provided by the invention.
Figure 4:
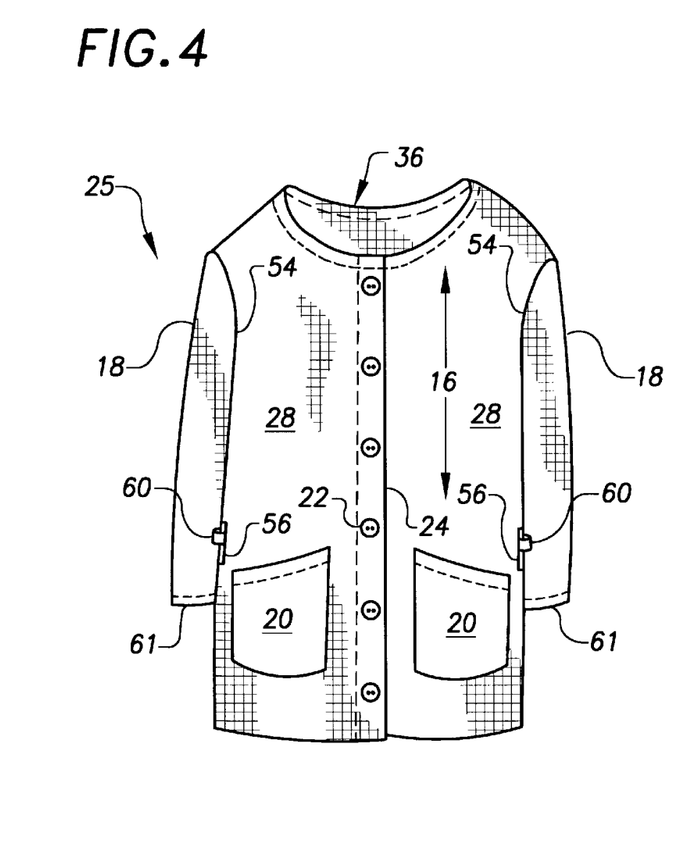
FIG. 4 is a front perspective view of an example jacket garment provided by the invention.

Three example garment embodiments in accordance with the invention, providing support, optionally but preferably concealment of, and access to, drainage apparatus like that shown in FIG. 1 are illustrated in FIGS. 2, 3, and 4. For clarity, the discussion will focus on an example directed to the use of fluidic drainage apparatus, but it is to be recognized that other fluidic tubing apparatus can be accommodated by the invention.

The example garments shown in FIGS. 2, 3, and 4 reflect a particular advantage provided by the invention in that they are conventional top clothes, i.e., not undergarments, and thus can be worn in public, as conventional clothing, without the need for additional clothing to conceal either the garments or the drainage apparatus, while at the same time providing support and access to the apparatus. The particular details of the support, concealment, and drainage apparatus access features of the garments are described in detail below.

First turning to the general garment design, the garments of the invention, examples of which are shown in FIGS. 2, 3, and 4, all are provided with a torso portion 16, arm holes that optionally are provided with sleeve portions 18, and at least one apparatus support, e.g., a support pocket 20, located at a convenient location, e.g., generally near to or at the front or a side of the torso portion 16, on the outside of the garment. Fasteners 22 can be provided to secure front mating edges of a front closure 24 of the torso portion, if such are included, as is preferable. The mating edges of a front closure 24 are preferable in that the front closure enables a garment to be readily and easily put on or removed and allows for repeated access and ease of examination by a health professional. This front closure allows patients to dress and undress themselves without assistance, enabling independent self-care in a manner that can enhance and speed up the recovery period.

Preferably, the torso portion, sleeve portions, and pockets or other supports are formed of a fabric having suitable characteristics for the patient. In general, for example, the selected fabric preferably is smooth textured and soft when placed against the skin to enable wearing of the garments immediately after a medical procedure as well as at the time of discharge from the hospital. The fabric optimally has a degree of opacity to provide the patient with a sense of privacy and modesty. Additionally, the fabric preferably is of low cost and high quality, easily worked, and highly durable, having an ability to hold up through numerous launderings. It further can be preferred that the fabric be free of synthetic materials, dyes, and chemical treatments that could cause an allergic reaction. For many garment configurations and applications, a cotton/polyester blend fabric is preferred. It is to be recognized, however, that many types of fabric can be utilized, provided that the fabric can accommodate the desired drainage apparatus concealment, support and access features of the garments of the invention.

Figure 10A:
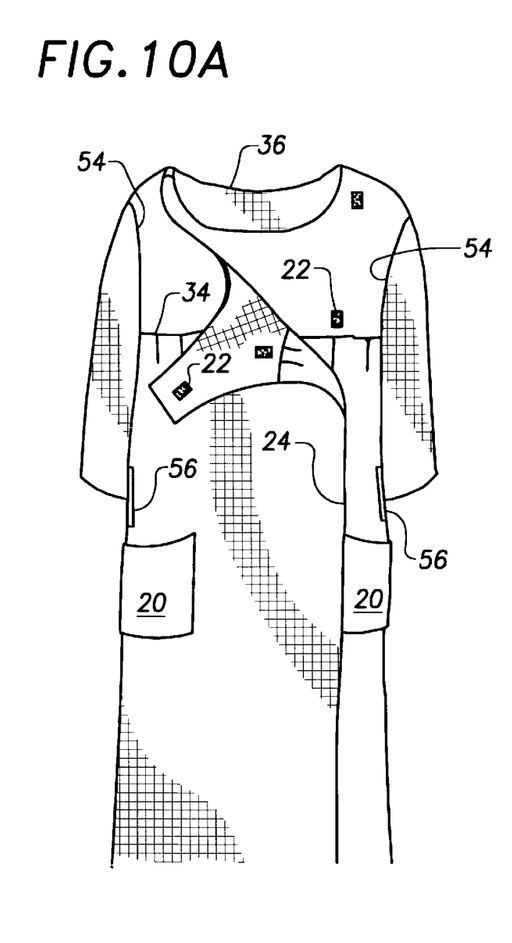
FIGS. 10A and 10B are one-quarter and back perspective views, respectively, of the house coat garment of FIG. 1.
Figure 10B:
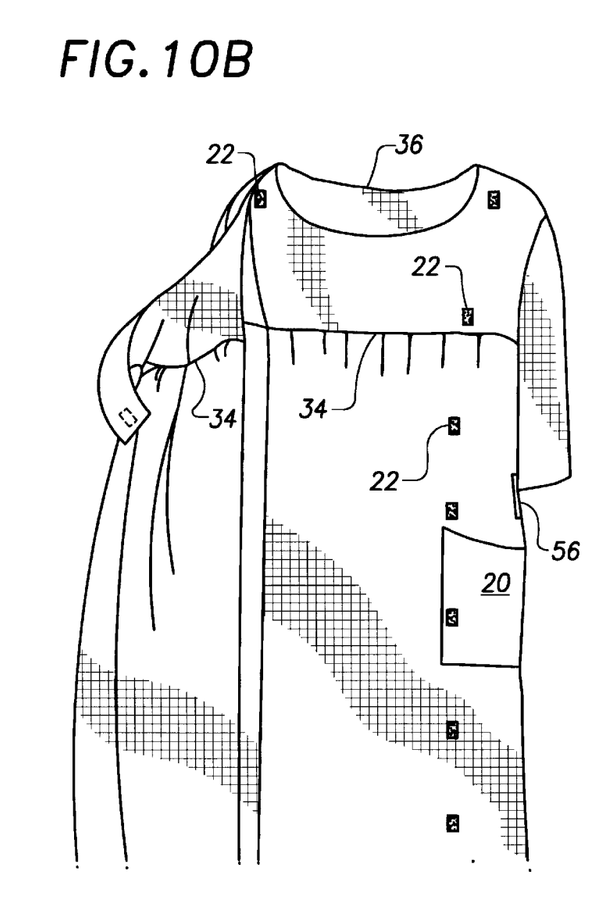

Referring now in more detail to the garment features provided by the invention, there are shown in FIGS. 2, 10A, and 10B details of the first example garment embodiment, worn as, e.g., a hospital gown housecoat, or dress 21, called the Bust Duster©. The torso portion 16 of the housecoat 21 can be formed of several pieces of fabric, preferably including one main panel 26. This main panel 26 extends from the front of the body around to the back of the body and then around to the front again. In one example configuration, a front yoke is provided with an attached facing 30, and similarly a back yoke is provided with an attached facing 32. A gathering 34, preferably above the bust line, is provided at the facing attachment locations. With this configuration, the housecoat 21 extends from a neckline 36 to a hemline 38, preferably which falls below the patient's knees.

The front closure 24 of the torso portion 16 is optionally and preferably positioned to produce a substantially overlapping fabric relationship across the garment front as shown in FIG. 10B, resulting in a doubling of the fabric at the garment front. This fabric overlap is advantageous in preventing open gaps during normal wear as well as in protecting the wearer from undue exposure, by increasing the garment's opacity. At the front closure 24 the fabric can be secured by at least one fastener 22, and more preferably by a plurality of fasteners, spaced along the closure between the neckline/shoulder to a lower point, e.g., the hemline. It can be preferred that if included, each fastener be provided as a cooperating material made from a hook and loop pile arranged on the fabric so as to cooperate with each other, as sold under the trademark Velcro™, or other suitable fastener arrangement. The fasteners 22 can also be provided as any conventional on-demand fastener, e.g., as a hook and eye, button and button hole, spindle and eyelet, snap, or other suitable fastener.

Figure 8A:
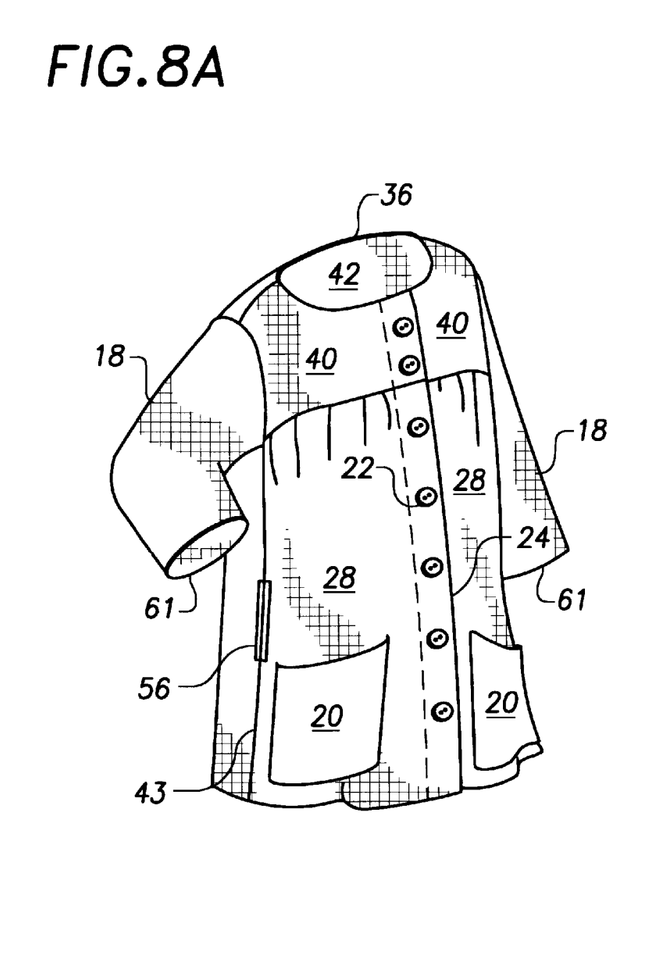
FIGS. 8A and 8B are one-quarter and back perspective views, respectively, of the casual top garment of FIG. 3.
Figure 8B:
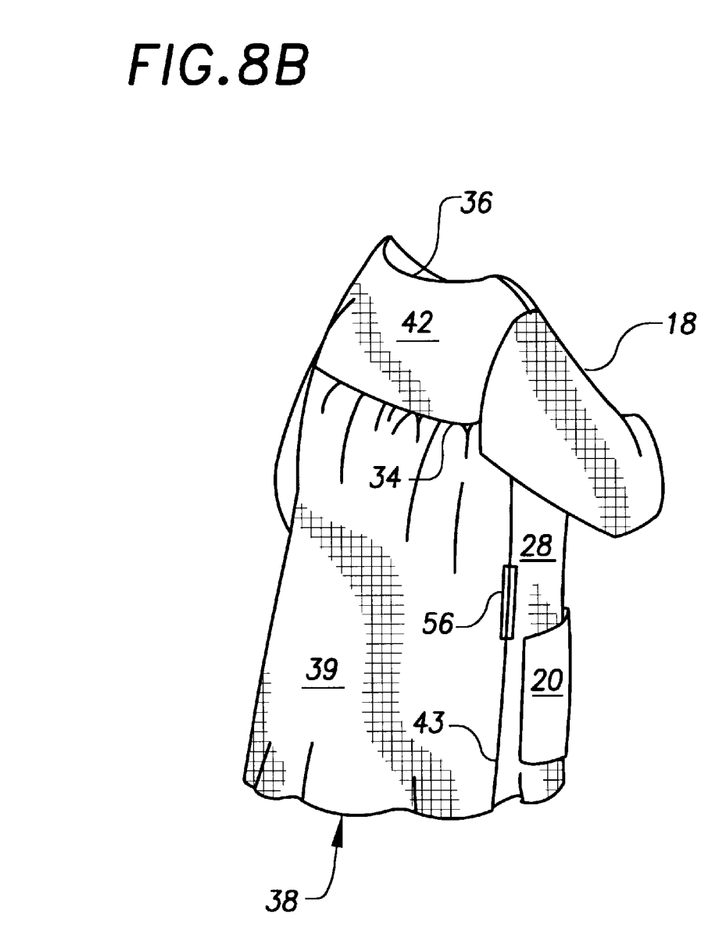

FIGS. 3, 8A, and 8B illustrate details of a second garment embodiment, a casual top 23, called the Smock Top©, worn with, e.g., slacks or a skirt. Preferably, the casual top 23 is formed of several pieces of fabric, including, e.g., two front panels 28, two front yokes with attached facings 40, a back panel 39, and a back yoke also with an attached facing 42. With this configuration, the casual top extends from, e.g., a neckline 36 to a hemline 38 that falls, e.g., to approximately to the top of the hip bone. The yokes are attached to the torso portion by a gathering that is preferably above the bust line. The back panel 39 is secured to the two front panels 28 at a side seam allowance 43 extending under the sleeve portions 18. The two front panels can be secured to each other at the front closure 24 by at least one, and preferably a vertically spaced plurality, of fasteners 22. The fasteners can be provided as a hook and loop pile fastener sold under the trademark Velcro™, or other fastener configuration in the manner described above.

Figure 9A:
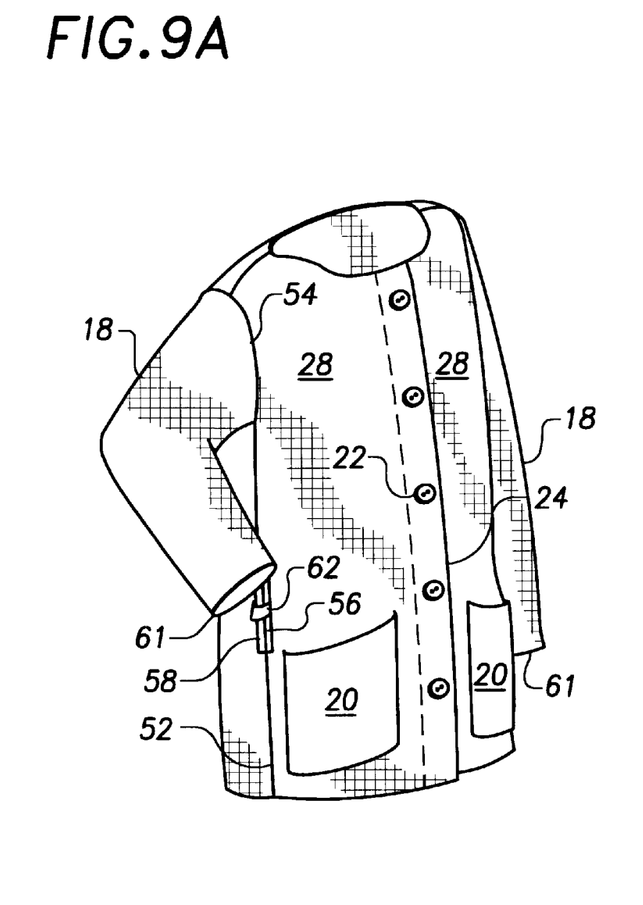
FIGS. 9A and 9B are one-quarter and back perspective views, respectively, of the jacket garment of FIG. 4.
Figure 9B:
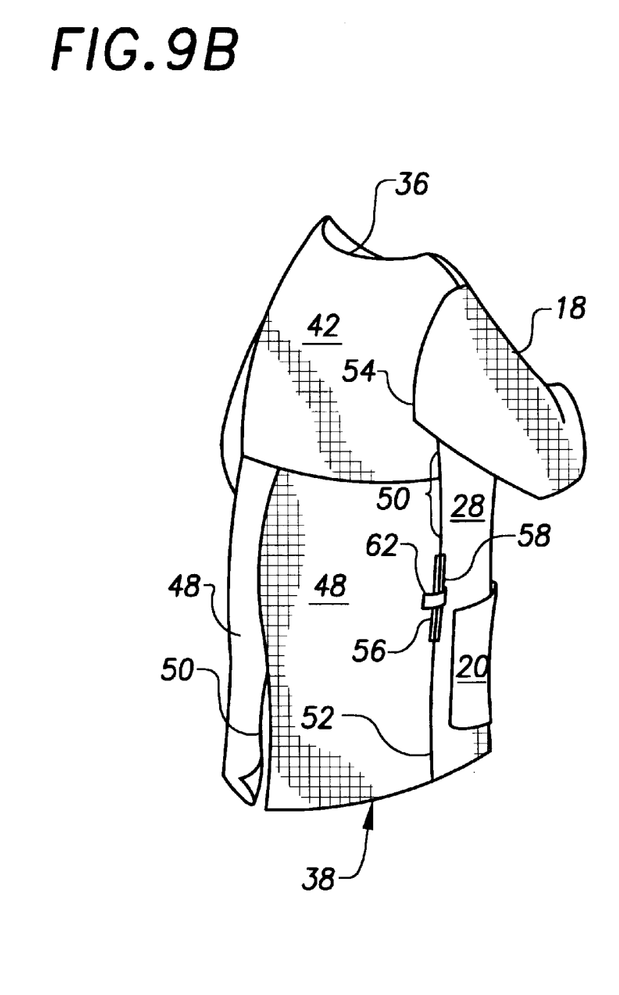

FIGS. 4, 9a, and 9B are illustrative of details of a third garment embodiment of the invention, here as a jacket configuration 25, called the Shirt Jacket©. The preferred jacket design is formed of several pieces of fabric, including, e.g., two main front panels 28 and two front collar facings, a back yoke 42 and back collar facing, and two back panels 48. In one example configuration, the two back panels are secured to each other along about the top ⅓ of the total length of the panels, forming a preferential kick pleat 50 at the bottom of the panels. The tops of the back panels are attached to the bottom seam allowance of the back yoke 42. The two back panels are also secured at a side seam allowance 52 under the sleeve portions 18. The two front panels 28 can be secured at a front closure 24 by at least one, and preferable a spaced plurality, of fasteners 22 like those described above. With this configuration, the jacket 25 extends down from a neckline 36 to a hemline 38 that falls, e.g., between the hips and thighs.

Particularly advantageous features of the garments of the invention include the gathering 34 above the bust line of the house coat 21 and casual top 23, as well as the preferential kick pleat 50 of the jacket 25. The gathering 34 above the bust line serves two important functions. First, it assists in masking partial or even significant disfigurement caused by, e.g., surgery. This ability to aid in projecting a normal or pre-surgical figure is fundamental to maintaining a high level of confidence and strong sense of self-esteem. These are invaluable qualities for enhancing the recovery process. In addition, the construction of this gathering allows for a roomier and looser fit at the area of the body where the patient often experiences edema and pain from surgery and the attachment of drainage apparatus. Moreover, the gathering design ensures that the wearer is able to move within the garment without exerting pressure on the drainage tubes that might cause the tubes to be detached from the body. The preferential kick pleat of the jacket similarly is notable in its ability to enhance range of movement, as well as to provide a more professional image than the house coat and casual top, and to provide a slimmer image for the more full-figured wearer.

Referring back to FIGS. 2, 3, and 4, in accordance with the invention, if sleeves are to be included on the garments, it can be preferred to provide the sleeve portions 18 of the garments with a drop-shoulder sleeve opening 54, as shown in the figures, that preferably extends beyond a conventional shoulder seam and that is wider than a conventional sleeve opening. The sleeves 18 are secured to the upper edge of the torso portion 16 which extends to the drop-shoulder sleeve opening 54. The sleeves 18 optionally but preferably do not extend to the wrist and instead end at the forearm to create a three-quarter-length sleeve. The forearm opening 61 is preferably wider than a conventional forearm opening, and is preferably suitably hemmed.

With a drop-shoulder sleeve opening 54 that is below a conventional shoulder seam, contact of the armpit of the wearer by the garment fabric can be avoided during dressing and undressing, thereby eliminating the chance of irritation of the skin of the armpit, the underarm, or the incision site. The wide sleeve and forearm openings maximize ease of dressing and undressing and maximize the wearer's mobility and comfort within the garment without constricting the wearer or exerting force on the drainage apparatus. These advantages take on particular significance with regard to the drainage apparatus support and access features of the garments, as described in detail below. The house coat, casual top, and jacket embodiments are provided as examples of garment configurations contemplated by the invention, but it is to be understood that a wide range of additional garment configurations can be employed in accordance with the invention. Whatever configuration is employed, the garment is to be wearable as top clothing, i.e., as an over garment like conventional clothing.

Figure 5:
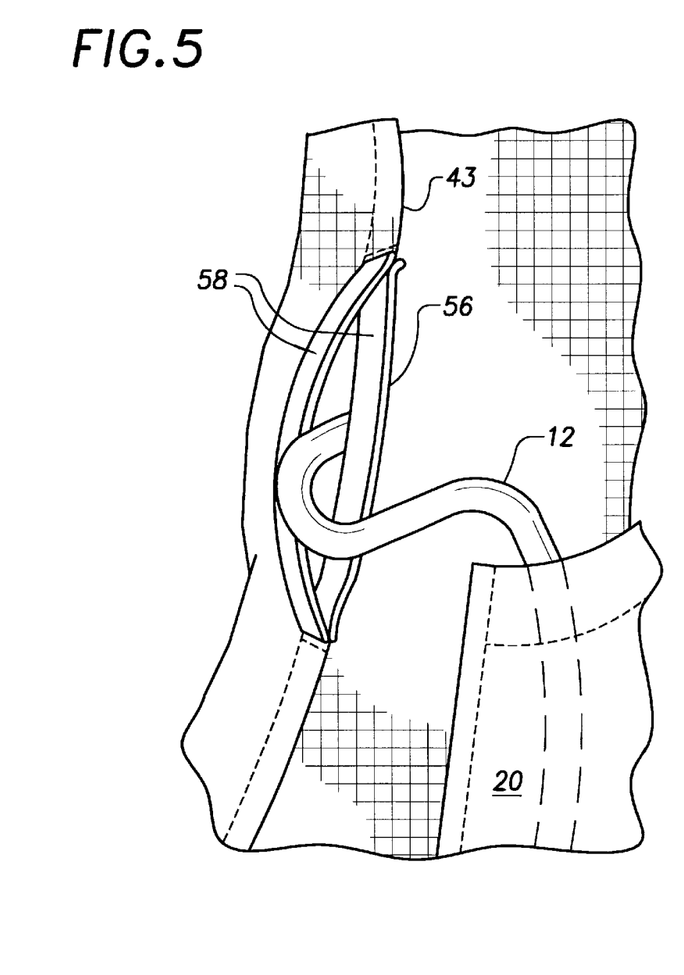
FIG. 5 is a perspective view of a first example garment opening and garment support pocket provided by the invention.

Referring to FIG. 5, whatever garment configuration is employed, in accordance with the invention the garment is provided with at least one opening 56 in the garment through which at least one drainage tube and other associated apparatus, such as a drainage receptacle, e.g., drainage bulb, can be drawn. The garment opening is provided specifically to enable the drawing of, e.g., the drainage tube and bulb out from under the garment and into the ambient environment outside of the garment, thereby providing access to the drainage apparatus through the garment. While only one garment opening is required by the invention, two or more openings can be provided at various locations on the garment, e.g., on the left and right sides of the garment, as prescribed by the drainage apparatus to be supported.

Figure 11A:
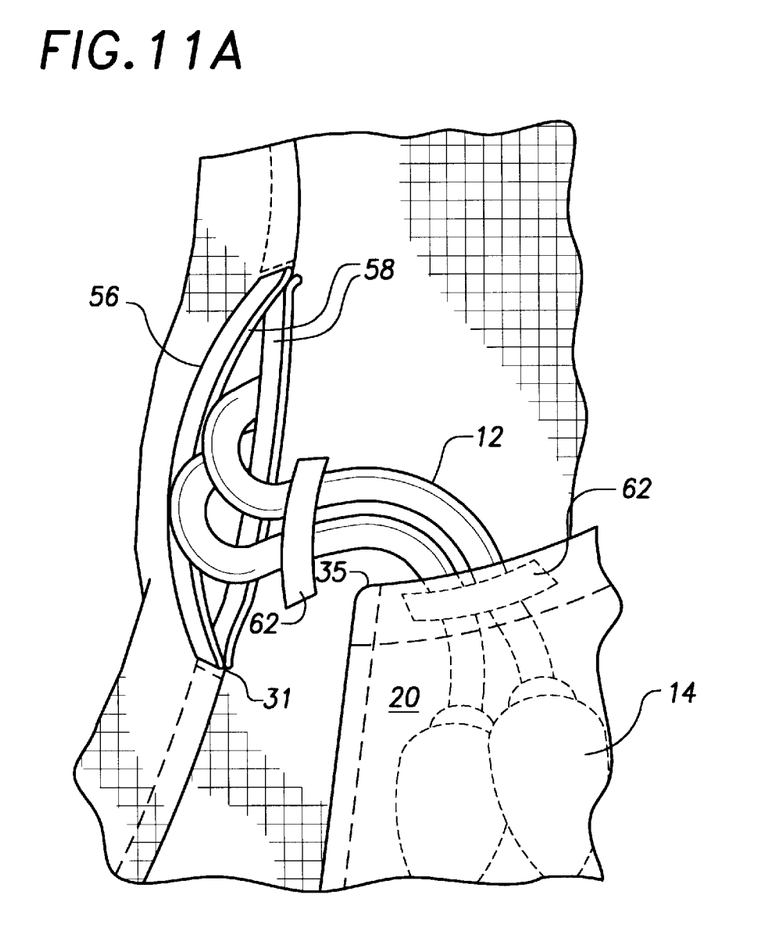
FIGS. 11A–11C are perspective views of additional example garment opening and garment support pocket configurations provided by the invention.

The garment opening or openings are preferably located at a point below the location of drainage tube attachment or attachments to the body and relatively close to a garment region, around the garment circumference, generally corresponding to the location of a drainage tube to be drawn through the opening. For example, for accommodation of drainage apparatus associated with a mastectomy, an opening is preferably provided at one or both of the left and right sides or left front and right front of the garment, both openings being a selected distance, e.g., between about five and about seven inches, below the underarm of the garment sleeve opening, whereby the opening is below the breast location of the garment torso portion 16, as shown in FIG. 4. This placement of the openings provides sufficient gravitational distance between the drainage tube incision attachment and the garment opening to promote proper fluid flow communication between incisions, drainage tubes, and collection bulbs. Each garment opening is preferably of a length, e.g., between about four and about eight inches, that will accommodate passage of apparatus associate with the tubes, e.g., a drainage receptacle such as a drainage bulb, through the opening. Preferably, each garment opening is also large enough to accommodate a desired number of drainage tubes, e.g., two tubes, as shown in FIG. 11, simultaneously positioned to extend through the opening.

In addition to being located circumferentially relatively near to incision points around the garment torso portion, the one or more garment openings are preferably located at a point or points on a garment that can be self-accessed by the garment wearer. Referring back to FIG. 5, for many applications and garment configurations, these two criteria can be met by providing each opening at a side seam location 43 a selected distance below the garment sleeve opening. This particular opening placement is not required by the invention; openings can be provided at any convenient point below a selected incision location, e.g., toward the center front of the garment. For ease of manufacture, as well as for styling considerations, location of garment openings at the side seams can often be preferred.

Figure 6:
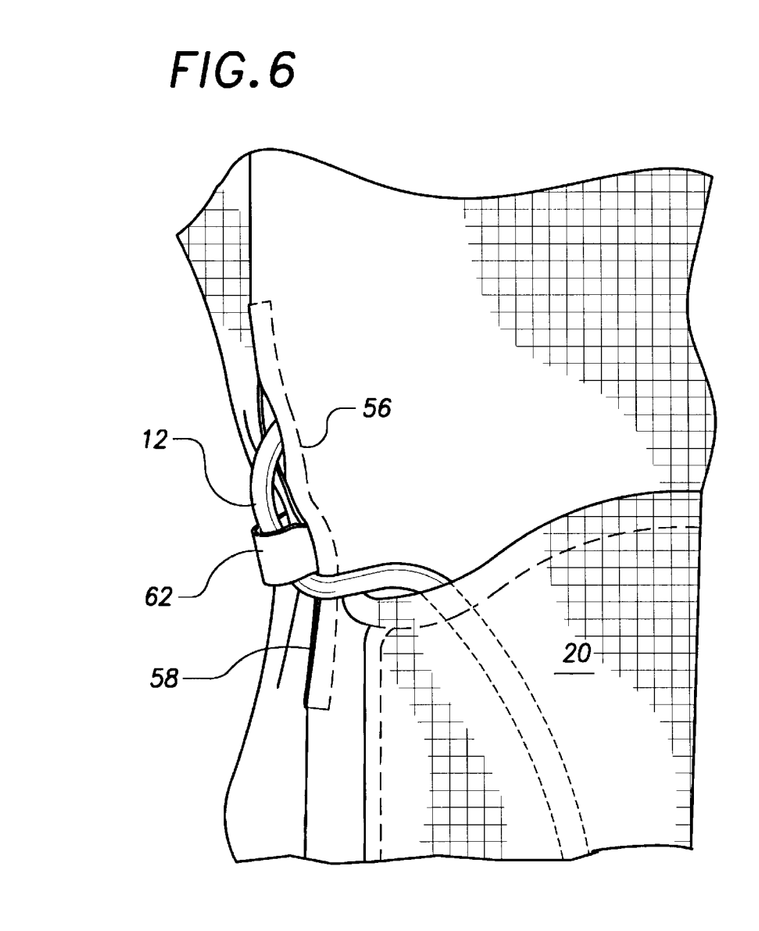
FIG. 6 is a perspective view of the garment opening and support pocket of FIG. 5, here including a tube tab fastener in accordance with the invention.

As shown in FIG. 5 and FIG. 6, in accordance with the invention, there can be provided one or more fasteners along the garment openings to enable closing of each opening around tubes positioned to extend through the opening, as shown in FIG. 6. Any suitable fastener or fasteners can be employed such as those described above. The invention does not require the use of opening fasteners; if desired, the garment opening can be employed without the use of a fastener or fasteners.

When an opening fastener is to be employed, hook and pile loop fasteners 58, such as hook and loop pile fasteners sold under the trademark Velcro™, can be preferred for many configurations for their ability to accommodate an arbitrary tube placement along the length of the opening and to securely seal the opening on either side of the tube. Given the use of a hook and pile loop fastener configuration, it can be preferred to locate openings at garment side seams. In this scenario, the side seam allowance connecting the back and front panels of the garment is preferably made larger than that conventionally employed, to here allow for the attachment of the hook and pile loop fasteners along the seam at each side of the opening, such that the fasteners can adhere to the adjacent inner surface of the seam opening. Whatever fasteners are employed, they preferably can be opened on-demand to facilitate the drawing through of the drainage apparatus. It is further contemplated by the invention that the configuration of fasteners be arranged such that when the drainage apparatus is no longer required, the opening can optionally be substantially completely closed along the garment opening to form a conventional seam or other region of the garment. This extends the usefulness and longevity of the garment.

Referring now more particularly to FIG. 6, there is shown an optional but preferred feature of the invention, namely, a tab fastener 62, provided at a point on the outer surface of the garment over which a drainage tube will extend, and having a tab that can be secured around a drainage tube or tubes for immobilizing the tubing. This can reduce or eliminate a risk of displacement of drainage tubes and/or accidental opening of drainage collection bulbs. For many garment configurations, it can be preferred to locate the tab fastener 62 at a point along the garment opening 56. Once the garment is positioned on the body, the drainage tubes and bulbs can be drawn through the garment opening or openings and tab fasteners 62 secured around the tube or tubes. The tab fastener can conveniently be constructed of the garment fabric itself and attached at the garment opening, e.g., a side seam, during construction of the garment. In one preferred configuration, a suitably-sized piece of hook and pile loop fastener material is attached to the underside of the tab fastener tab, with a mating piece attached at a corresponding position on the garment, for cooperating with the tab fastener to secure a tube or tubes to the garment.

Figure 7:
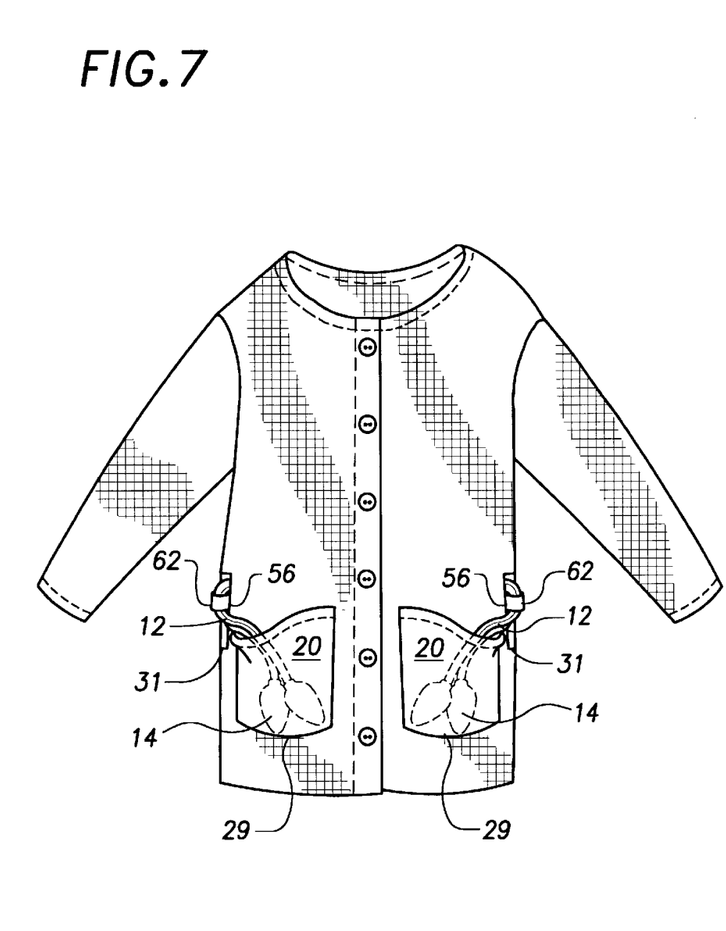
FIG. 7 is a front perspective view of the jacket of FIG. 4, here shown with drainage tubes drawn through the garment opening and fluid collection bulbs supported by garment support pockets, both in accordance with the invention.

Referring now to FIG. 7 and FIG. 11A, there is shown the drainage apparatus support 20 provided by the invention, here shown, for example, as a pocket or pockets. The drainage apparatus support of the invention, in whatever configuration taken, is provided on the outside surface of the garment fabric or other material, at a location that retains, preferably conceals, and supports the drainage collection receptacles, e.g., collection bulbs 14. The support or supports 20 are preferably positioned a distance, e.g., between about one to about three inches, below the garment opening 56 to allow the collection bulbs to rest in a secure manner, as shown in FIG. 7. This effectively eliminates constriction of the drainage tubes and minimizes the danger of displacing or rupturing the collection bulbs and drainage tubes.

The distance between the garment opening and the support is also preferably set so that positive fluid flow communication between the drainage tubes and collection bulbs is enhanced and promoted. In particular, as shown in FIG. 7, the collection bulbs 14, when in the supports 20, here pockets, preferably are maintained lower than the point at which the drainage tubing is positioned to extend through the garment opening so that gravity effectively inhibits backing up of fluid into the tubing. For example, as shown in the figure, the bottom 29 of the pocket is lower than the bottom 31 of the garment opening 56. The collection bulb or other receptacle can rest on its side in the support, but at least one point of the receptacle is optimally lower than the point at which the drainage tubing is positioned to extend through the opening. The geometry and location of the support on the garment is thus preferably determined to enable this configuration when the garment is worn, based on the length of the tubing and the size of the garment wearer.

As shown in FIGS. 7 and 11A, the supports 20 can be configured to accommodate a plurality of drainage bulbs 14; with the provision of two or more supports 20, four or more drainage tubes and bulbs can then be maintained. To accomplish this, for many applications and garment configurations, it can be preferred to provide the supports as pockets on the outside front panels of the torso portion of the garment. This placement enables self-positioning and maintenance of multiple sets of drainage apparatus by the garment wearer while at the same time concealing all of the apparatus sets. As shown in FIG. 7, pocket supports can be optionally but preferably be provided as slanted patch pockets, preferably having reinforced stitching, for optimal distribution of the weight of fluid-filled bulbs. As the fluid draining process continues, the weight of the collection bulbs increases as fluid collects and accumulates in the bulbs. It is found that this increasing bulb weight is optimally supported by reinforced, oversized, slanted patch pockets.

Figure 11B:
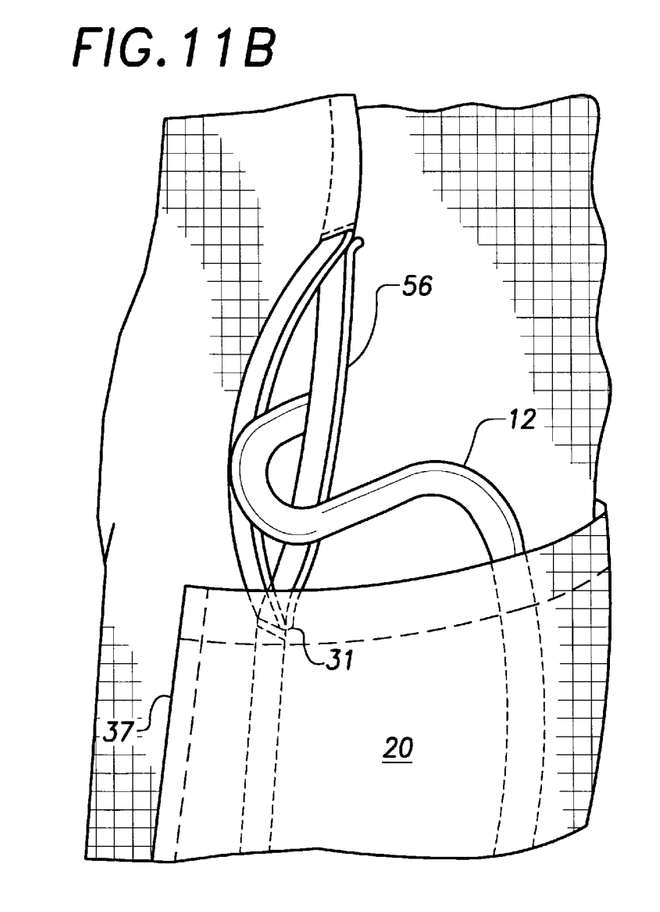
Figure 11C:
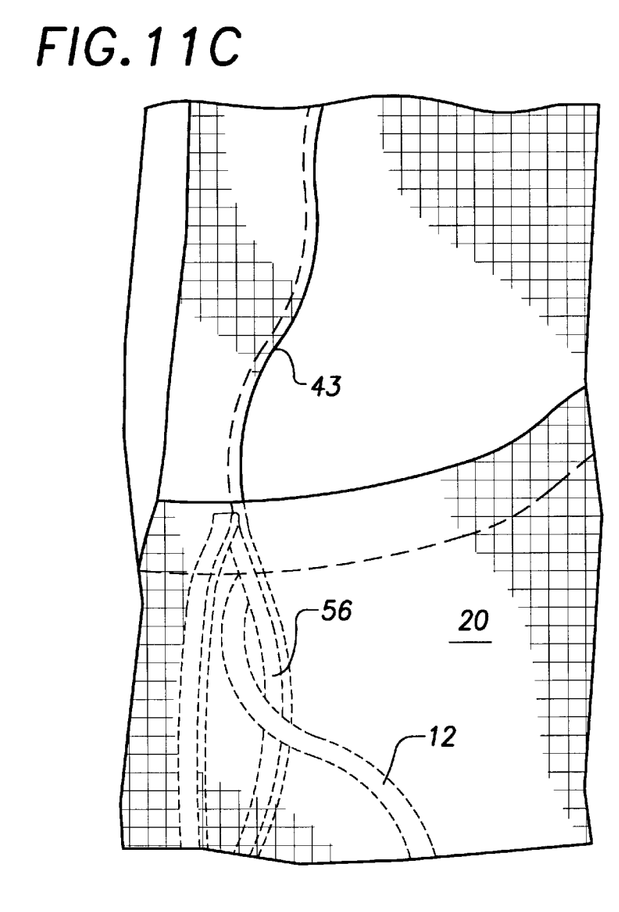
Figure 11D:
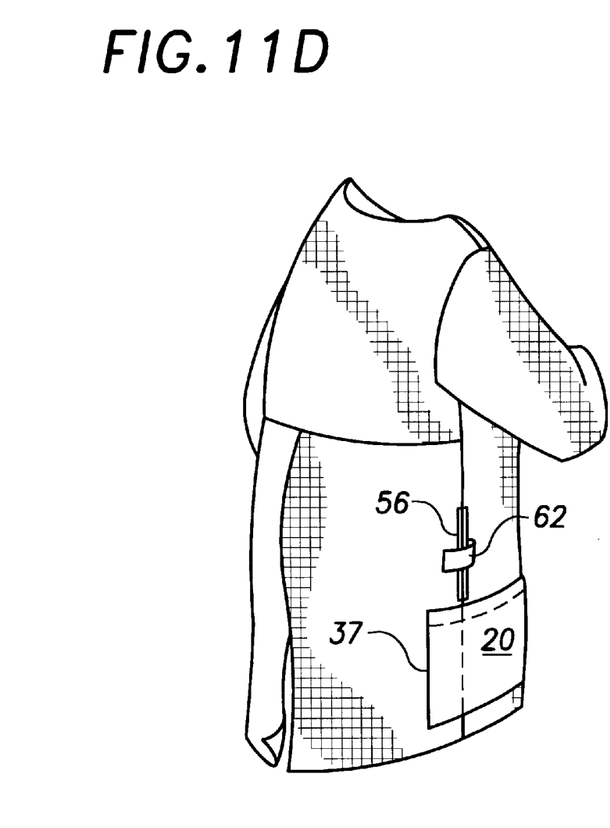
FIGS. 11D–11E are back perspective views of additional example garment opening and garment support pocket configurations provided by the invention.

Turning to FIGS. 11A–E, there are shown examples of a garment opening 56 and corresponding support pocket 20 for a configuration in which the garment opening is provided along a side seam of the garment. Although the example configurations of FIGS. 11A–E particularly address a scenario in which the garment opening is located at a side seam, it is to be recognized that such is not required for these configurations; for any positioning of the opening on the garment the pocket support location can be adjusted in the manner described. In a first example, shown in FIG. 11A, the bottom 31 of the garment opening 56 is below the top 35 of the support pocket 20. With this correspondence, then as shown in FIG. 11B, the side edge 37 of the support pocket 20 can extend over the garment opening 56; here the bottom 31 of the garment opening is covered by the pocket 20. Alternatively, as shown in FIG. 11D, the side edge 37 of the support pocket 20 can extend beyond the garment opening 56 while the pocket remains entirely below the garment opening.

Figure 11E:
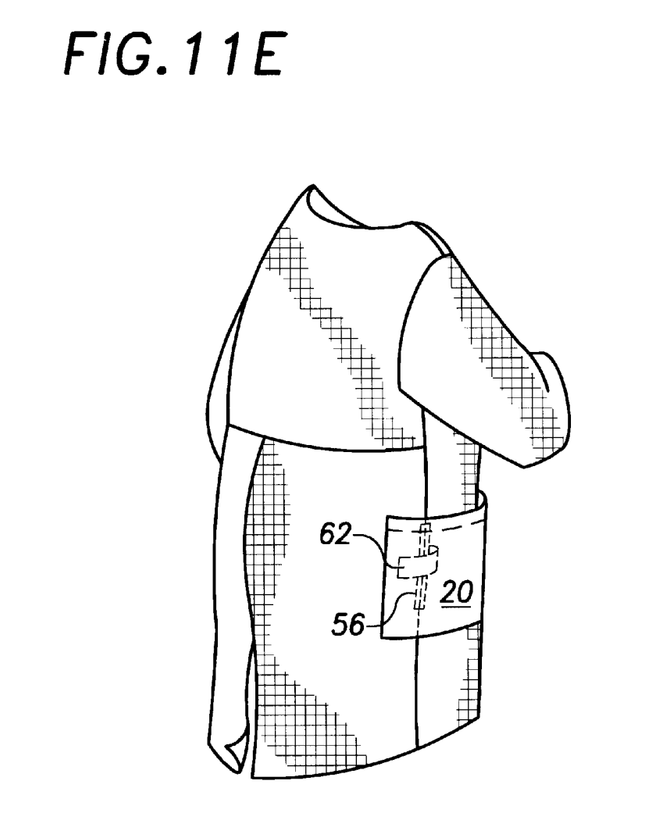

Referring to FIG. 11C and FIG. 11E, in a further configuration, the garment opening 56 can be provided entirely within the support pocket 20, whereby the drainage apparatus is entirely concealed by the support pocket while remaining accessible within the pocket. For many applications this can be a preferred configuration because the garment appears completely conventional as top clothes while the drainage apparatus is effectively completely hidden but fully supported and accessible at the outside of the garment.

As shown in FIG. 11E, if desired, a tube tab fastener 62 can be provided in any of these support configurations for securely immobilizing drainage tubes on the garment. Although the tab fastener is shown in FIG. 11E as being provided at the location of the garment opening 56, such is not required by the invention. As shown in FIG. 11A, a tab fastener 62 can be provided on the outside of the garment at a point away from the garment opening 58, for example on the front of the garment between the garment opening and drainage pocket support, and/or within the pocket support itself. Multiple tab fasteners can be employed, as desired, for maximizing the immobilization of the drainage apparatus on the garment.

The invention contemplates a wide range of alternative configurations for drainage apparatus support pockets and other support designs. If provided as a pocket, the support need not be a slanted, top-open patch pocket; a side-open pocket or other pocket configuration can be employed. One pocket can be provided to support drainage apparatus from both sides of the body, or multiple pockets can be provided at selected locations around the garment. Whatever pocket configuration is selected, it preferably is positioned such that positive fluid flow communication between drainage tubes and collection bulbs is maintained.

One or more of the support pockets can be lined with an impervious material, e.g., a plastic or plastic-coated material, to protect the garment against spillage of the fluid from the drainage bulbs in the pockets. One or more open on-demand fasteners can be provided on the support pocket to enhance support of the drainage apparatus in the pockets. Any of the various fasteners described above can here be employed. Additionally, a storage pocket can be provided over the support pocket for use in the manner of a conventional pocket.

Although a pocket is the preferred drainage support configuration contemplated by the invention, a range of alternative support configurations can be employed. For example, a support compartment, pouch, band, strap, sleeve, cup, tie, or other support configuration can be provided on the outside of the garment, in correspondence to a garment opening, for supporting drainage collection bulbs or other receptacles. Preferably the support configuration conceals the collection receptacles while maintaining access to the receptacles. Equally important, the support configuration preferably is located such that collection receptacles are supported at a point lower than the bottom of the drainage tube, when the tube is hanging down, to eliminate a risk of fluid back flow from a receptacle into a tube.

Whatever support configuration is employed, in accordance with the invention the garment is configured to accommodate the selected support. The house coat, casual top, and jacket garments described above are only a few examples of the wide range of garment configuration contemplated by the invention. The invention is not limited to a particular garment design; rather, the invention requires a selected garment design to include a garment opening through which fluidic tubes and associated apparatus, e.g., receptacles, can be drawn, and a drainage support for retaining and providing access to the apparatus, on the outside the garment.

As explained previously, it is preferred that the support conceal the drainage apparatus on the outside of the garment. It has been noted that the length of a patient's recovery period associated with surgery is often linked to a patient's sense of well-being and personal dignity. If a patient feels that they are putting forth their best appearance, their recovery may be enhanced. By concealing the drainage apparatus in a support, e.g., a support pocket, the garments of the invention look no different than conventional top clothes and are worn as conventional top clothes. This enables and allows the garment wearer to accomplish every day tasks in public in a manner that does not emphasize their recovering condition. The allowance of the garments of the invention for fashion, modesty, and discretion, as well as accessibility, make them particularly well-suited as an aid in the recovery process.

With the garments of the invention, drainage apparatus can be worn comfortably and securely in a location that is convenient for maintenance and secure in preventing liquid backflow through drainage tubes to the incision site. As a patient begins the recovery process and their mobility increases, there is a need for a garment that allows for painless and unhindered movement. The garments of the invention meet this need by freeing the hands of the wearer, by providing a support for the drainage apparatus, and by preventing inadvertent displacement of tubing and/or leakage from collection receptacles.

The garments of the invention are particularly well suited for use by female patients who have undergone thoracic surgery such as, e.g., chest, breast, or underarm surgery. The garments are not, however, limited to such procedures. Indeed, the garments of the invention can be advantageously employed in conjunction with any medical procedure, thoracic or otherwise, that requires the support of a drainage apparatus attached to the body. Furthermore, the garments of the invention can be advantageously employed for supporting apparatus other than drainage apparatus, such as chemotherapy apparatus, e.g., for supporting a chemotherapy supply to a port attached to the body. It is therefore to be understood that the garments of the invention are applicable to a wide range of conditions and apparatus, and can easily be adapted for use by youths and male as well as female patients. Furthermore, the ability to convert the garment openings to conventional seams extends the functionality of the garment to the entire treatment and recovery period, and beyond.

It is recognized, of course, that those skilled in the art may make various modifications and additions to the garments of the invention described above without departing from the spirit and scope of the present contribution to the art. Accordingly, it is to be understood that the protection sought to be afforded hereby should be deemed to extend to the subject matter of the claims and all equivalents thereof fairly within the scope of the invention.

We claim:

1. A garment comprising:

a torso portion of an extent sufficient to encircle a garment wearer's torso;

arm openings provided in the torso portion;

generally vertical and cooperating front torso portion edges providing a vertical front closure of the torso portion;

at least one garment opening below a breast location in the torso portion, the garment opening being of an extent sufficient to accommodate passage of a fluidic tube and a corresponding fluidic receptacle through the opening and to accommodate positioning of at least one fluidic tube extending through the garment opening; and at least one fluidic receptacle support located on an outside surface of the torso portion and having a receptacle support surface, the support surface being vertically below a point at which a corresponding fluidic tube would be positioned to extend through a corresponding garment opening.

2. The garment of claim 1 further comprising at least one garment opening fastener provided at a point along the garment opening to close the opening around a fluidic tube positioned to extend through the opening.

3. The garment of claim 2 wherein the garment opening fastener is provided along the garment opening to substantially fully close the opening.

4. The garment of claim 1 further comprising at least one fluidic tube fastener located on the outside surface of the torso portion and having a tab to secure at least one fluidic tube to the torso portion.

5. The garment of claim 4 wherein the fluidic tube fastener is located at a point along the garment opening.

6. The garment of claim 1 wherein the garment opening is located at a point along a seam of the torso portion.

7. The garment of claim 1 wherein the fluidic receptacle support comprises a receptacle support pocket.

8. The garment of claim 7 wherein the receptacle support pocket comprises a patch pocket.

9. The garment of claim 8 wherein the receptacle support pocket comprises a slanted pocket.

10. The garment of claim 7 wherein the receptacle support pocket includes reinforced pocket seam stitching.

11. The garment of claim 7 wherein the receptacle support pocket extends sufficiently over the torso portion outer surface to substantially conceal a fluidic receptacle.

12. The garment of claim 11 wherein the receptacle support pocket extends sufficiently over the torso portion outer surface to substantially conceal a plurality of fluidic receptacles.

13. The garment of claim 7 further comprising at least one fluidic tube fastener located in the receptacle support pocket and having a tab to secure at least one fluidic tube to the torso portion.

14. The garment of claim 7 further comprising a pocket fastener on the receptacle support pocket for securing an open end of the pocket to the torso portion.

15. The garment of claim 7 wherein the receptacle support pocket includes a pocket bottom that is located on the garment torso portion vertically below a point at which a corresponding fluidic tube would be positioned to extend through a corresponding garment opening.

16. The garment of claim 7 wherein the receptacle support pocket extends over the torso portion a distance sufficient to cover at least a portion of the corresponding garment opening.

17. The garment of claim 16 wherein the receptacle support pocket extends over the torso portion a distance sufficient to substantially completely cover the corresponding garment opening.

18. The garment of claim 7 wherein the receptacle support pocket includes an interior pocket surface that is impervious to fluid.

19. The garment of claim 7 wherein the receptacle support pocket includes a storage pocket located on top of the support pocket.

20. A garment comprising:
a torso portion of an extent sufficient for encircling a garment wearer's torso;
arm openings provided in the torso portion;
generally vertical and cooperating front torso portion edges providing a vertical front closure of the torso portion;
an opening in a seam of the garment below a breast location in the torso portion, the seam opening being of an extent along the seam that is sufficient to accommodate passage of a fluidic tube and a corresponding fluidic receptacle through the opening and to accommodate positioning of at least one fluidic tube to extend through the side seam opening; and
at least one fluidic receptacle support pocket located on an outside surface of the torso portion, a bottom of the support pocket being vertically below a point at which a corresponding fluidic tube would be positioned to extend through a corresponding garment opening.

21. The garment of claim 1 wherein the fluid receptacle support comprises a receptacle compartment located on an outside surface of the torso portion and having a receptacle support surface, the support surface being vertically below a point at which a corresponding fluidic tube would be positioned to extend through a corresponding garment opening.

22. The garment of claim 1 wherein the fluid receptacle support comprises a receptacle pouch located on an outside surface of the torso portion and having a receptacle support surface, the support surface being vertically below a point at which a corresponding fluidic tube would be positioned to extend through a corresponding garment opening.

23. The garment of claim 1 wherein the fluid receptacle support comprises a receptacle sleeve located on an outside surface of the torso portion and having a receptacle support surface, the support surface being vertically below a point at which a corresponding fluidic tube would be positioned to extend through a corresponding garment opening.

24. The garment of claim 1 wherein the garment opening is located at a position around the torso portion that is self-accessible by the garment wearer.

25. The garment of claim 1 further comprising sleeve portions connected to the torso portion.

26. The garment of claim 25 wherein the sleeve portions are each connected to the torso portion at a drop-shoulder sleeve opening.

27. The garment of claim 1 further comprising a kick pleat located at a back region of the torso portion.

28. The garment of claim 1 wherein the torso portion includes a front yoke having a gathering located above a point generally corresponding to a garment wearer's bust line.

29. The garment of claim 1 wherein the cooperating front torso portion edges include at least one fastener at the front closure of the torso portion.

30. The garment of claim 1 wherein the cooperating front torso portion edges are of sufficient horizontal extent to horizontally overlap at the front closure of the torso portion.

31. A garment comprising:
a torso portion of an extent sufficient to encircle a garment wearer's torso;
arm openings provided in the torso portion;
generally vertical and cooperating front torso portion edges providing a vertical front closure of the torso portion;
at least one garment opening below a breast location in the torso portion, the garment opening being of an extent sufficient to accommodate passage of a fluidic tube and a corresponding fluidic receptacle through the opening and to accommodate positioning of at least one fluidic tube extending through the garment opening; and
at least one fluidic receptacle support means located on an outside surface of the torso vertically below a point at which a corresponding fluidic tube would be positioned to extend through a corresponding garment opening.

* * * * *